United States Patent [19]

Kawai et al.

[11] Patent Number: 4,833,129
[45] Date of Patent: May 23, 1989

[54] HYPOCHOLESTEROLEMICALLY AND/OR HYPOTRIGLYCERIDEMICALLY ACTIVE RNA FRACTIONS

[75] Inventors: Yasuo Kawai, Atsugi; Kazunaga Yazawa, Sagamihara, both of Japan

[73] Assignee: Kabushiki Kaisya Advance Kaihatsu Kenkyujo, Tokyo, Japan

[21] Appl. No.: 877,125

[22] Filed: Jun. 23, 1986

[30] Foreign Application Priority Data

Jul. 3, 1985 [JP] Japan ................... 60-144828

[51] Int. Cl.⁴ .................. A61K 31/70; C07H 21/02
[52] U.S. Cl. ............................... 514/44; 536/27
[58] Field of Search ........... 514/44; 536/27, 28, 536/29

[56] References Cited

U.S. PATENT DOCUMENTS

| | | | |
|---|---|---|---|
| 3,567,821 | 3/1971 | Nouvel | 424/104 |
| 4,190,649 | 2/1980 | Beljanski | 514/44 |
| 4,259,442 | 3/1981 | Gayral | 535/36 |
| 4,297,272 | 10/1981 | d'Hinterland et al. | 530/395 |
| 4,335,329 | 6/1982 | Beljanski | 536/27 |
| 4,357,323 | 11/1982 | Soma et al. | 424/180 |
| 4,389,392 | 6/1983 | d'Hinterland | 514/44 |
| 4,448,768 | 5/1984 | Coleman et al. | 424/85 |
| 4,536,496 | 8/1985 | Shimizu et al. | 514/54 |
| 4,579,733 | 4/1986 | Kawai et al. | 424/93 |
| 4,621,055 | 11/1986 | Kawai et al. | 424/95 |
| 4,687,764 | 8/1987 | Kawai et al. | 536/1.1 |
| 4,710,379 | 12/1987 | Kawai et al. | 424/93 |

FOREIGN PATENT DOCUMENTS

| | | |
|---|---|---|
| A-0013851 | 8/1980 | European Pat. Off. . |
| A-0029893 | 10/1981 | European Pat. Off. . |
| A-0101209 | 2/1984 | European Pat. Off. . |
| A-0115157 | 8/1984 | European Pat. Off. . |
| A-0132981 | 2/1985 | European Pat. Off. . |
| A-0186482 | 2/1986 | European Pat. Off. . |
| 0186482 | 7/1986 | European Pat. Off. .............. 514/44 |
| 2106154 | 8/1972 | Fed. Rep. of Germany . |
| 49-15280 | 4/1974 | Japan ..................... 536/29 |
| 0003100 | 1/1979 | Japan ..................... 514/44 |
| 0122723 | 4/1980 | Japan . |
| 56-12318 | 2/1981 | Japan . |
| 58-131917 | 2/1985 | Japan . |
| 930100 | 7/1963 | United Kingdom . |
| 2090846 | 7/1982 | United Kingdom . |

OTHER PUBLICATIONS

Nord et al., "Formation of Glycoside-Hydrolases by Oral Streptococci," Archs. Oral Biol., vol. 18, pp. 391–402 (1973).

(List continued on next page.)

*Primary Examiner*—Ronald W. Griffin
*Assistant Examiner*—Jenny Tou
*Attorney, Agent, or Firm*—Finnegan, Henderson, Farabow, Garrett & Dunner

[57] ABSTRACT

Hypocholesterolemically and/or hypotriglyceridemically active RNA fractions having the following characteristics:

(a) Molecular weight by gel filtration: 2,000 ± 1,000
(b) Base composition ratio of nucleic acid: uracil: guanine: cytosine: adenine = 13.0: 16.0: 16.0: 10.0
(c) Infrared absorption sepctrum: shown in FIG. 2
(d) Physiological characteristics: having a hypocholesterolemic and/or hypotriglyceridemic activity in mammals.

These hypocholesterolemically and/or hypotriglyceridemically active RNA fractions can be prepared by cultivating a microorganism belonging to the genus Streptococcus in an adequate culture medium therefor; and collecting the hypocholesterolemically and/or hypotriglyceridemically active RNA fractions from the cultured cells of the microorganism. These hypocholesterolemically and/or hypotriglyceridemically active RNA fractions can be used as an active ingredient of a hypocholesterolemic or hypotriglyceridemic pharmaceutical composition together with a pharmaceutically acceptable carrier therefor to form a hypocholesterolemic or hypotriglyceridemic pharmaceutical composition, which is suitable for oral administration to mammals.

8 Claims, 3 Drawing Sheets

OTHER PUBLICATIONS

Moore et al., "Cell–Free Protein Synthesis: Effects of Age and State of Ribosonal Aggregation," Science, vol. 154, pp. 1350-1353 (1966).

Chem. Abstracts, vol. 83, No. 1, Jul. 7, 1975.

Herson et al., "Protein Synthesis in Cell–Free Extracts of Streptococcus Faecalis", J. of Bacteriology, vol. 100, No. 3, pp. 1350-1354, (1969).

Rao et al., "Influence of Milk and Themophilus Milk on Plasma Cholesterol Levels and Hepatic Cholesterogenesis in Rats", J. of Food Sci., vol. 46, pp. 1339-1341, (1981).

Salvioli et al., "Bile Acid Transformation by the Intestinal Flora and Cholesterol Saturation in Bile," Digestion, vol. 23, pp. 80-88.

Hussain et al., "Activation of Lipolytic Activity of Streptococcus Cholesterogenesis in Rats," J. of Food Sci., vol. 46, pp. 1339-1340, (1981).

Rall et al., "Human Apolipoprotein E," J. Biol. Chem., vol. 275(8), pp. 4171-4178, (1982).

Slobodskaya et al., "Comparison of Hypocholesterolemic Effect . . . ", Biol. Abstract, 76(10), (1983).

Bergy's Manual of Determinative Bacteriology, 8th Ed., Williams and Williams, 1974.

"Studies on Streptococci, I. Distribution of Fecal Streptococci in Man," Microbiol. Immunol. 25(3), 257-269, 1981.

"Studies on Streptococci, II. Colonization of Lactic Acid Bacteria Isolated from Rats and Humans in the Gastrointestinal Tract of Rats," Microbiol. Immunol. 26(5), 363-373, 1982.

"Distribution and Colonization of Human Fecal Streptococci," The American J. of Clinical Nutrition, 33, Nov. 1980, pp. 2458-2461.

"Intestinal Enzyme Activities in Germfree, Conventional, and Gnotobiotic Rats Associated with Indigenous Microorganisms, Infection and Immunity," Mar. 1978, pp. 771-778.

"Quantitative and Qualitative Altenation of Mucosal Alkaline Phosphatase by Indigenous Intestinal Microbes in the Upper Digestive Tract of the Rat," the American J. of Clinical Nutrition, 32, Jan., Intestinal Enzyme Activities in Germfree, Conventional, and 1979, pp. 187-188.

"Intestinal Microflora and Aging: Age-Related Change of Lipid Metabolism in Germfree and Conventional Rats," Mechanisms of Aging and Development, 16 (1981), pp. 149-158.

"Intestinal Microflora and Aging: Age-Related Change of Enzymes in the Liver and the Small Intestine of Germfree and Conventional Rats," Mechanisms of Aging and Development, 17 (1981), pp. 173-182.

HYPOCHOLESTEROLEMICALLY AND/OR HYPOTRIGLYCERIDEMICALLY ACTIVE RNA FRACTIONS

BACKGROUND OF THE INVENTION

1. Field of the Invention

The present invention relates to novel hypocholesterolemically and/or hypotriglyceridemically active ribonucleic acid (i.e., RNA) fractions, a process for preparing the same, a hypocholesterolemically and/or hypotriglyceridemically active pharmaceutical composition containing the same, and a method for reducing blood cholesterol and triglyceride in mammals.

2. Description of the Related Art

As is well-known in the art, several pharmaceutical preparations such as clofibrate and its related preparations have been proposed as therapeutical medicines for atherosclerosis or hyperlipidemia, considered to be a typical middle-aged or geriatric disease. However, the desired purposes are not fully satisfied by these known medicines from the viewpoint of, for example, pharmacological effects and side-effects, and there is a strong demand for the development of safe and more effective medicines.

SUMMARY OF THE INVENTION

Accordingly, an object of the present invention is to provide novel hypocholesterolemically and/or hypotriglyceridemically active RNA fractions which can be safely administered to mammals.

Another object of the present invention is to provide a process for preparing novel hypocholesterolemically and/or hypotriglyceridemically active RNA fractions capable of effectively reducing blood cholesterol and triglyceride in mammals.

A further object of the present invention is to provide a hypocholesterolemic and/or hypotriglyceridemic pharmaceutical composition containing, as an active ingredient, novel RNA fractions.

A still further object of the present invention is to provide a method of reducing blood cholesterol and triglyceride in mammals.

Other objects and advantages of the present invention will be apparent from the description set forth hereinbelow.

In accordance with the present invention, there are provided hypocholesterolemically and/or hypotriglyceridemically active RNA fractions having the following characteristics:

(a) Molecular weight by gel filtration: 2,000±1,000
(b) Base composition ratio of nucleic acid: uracil:guanine:cytosine:adenine=13.0:16.0:16.0:10.0
(c) Infrared absorption spectrum: shown in FIG. 2
(d) Physiological characteristics: having a hypocholesterolemic and/or hypotriglyceridemic activity in mammals.

These hypocholesterolemically and/or hypotriglyceridemically active RNA fractions can be prepared by cultivating a microorganism belonging to the genus Streptococcus in an adequate culture medium therefor; and collecting the hypocholesterolemically and/or hypotriglyceridemically active RNA fractions from the cultured cells of the microorganism. The present hypocholesterolemically and/or hypotriglyceridemically active RNA fractions can be used as an active ingredient of a hypocholesterolemic or hypotriglyceridemic pharmaceutical composition together with a pharmaceutically acceptable carrier therefor, to form a hypocholesterolemic and/or hypotriglyceridemic pharmaceutical composition which is suitable for oral administration to mammals.

BRIEF DESCRIPTION OF THE DRAWING

The present invention will be better understood from the description set forth below with reference to the accompanying drawings in which.

DESCRIPTION OF THE PREFERRED EMBODIMENTS

Figure 1:
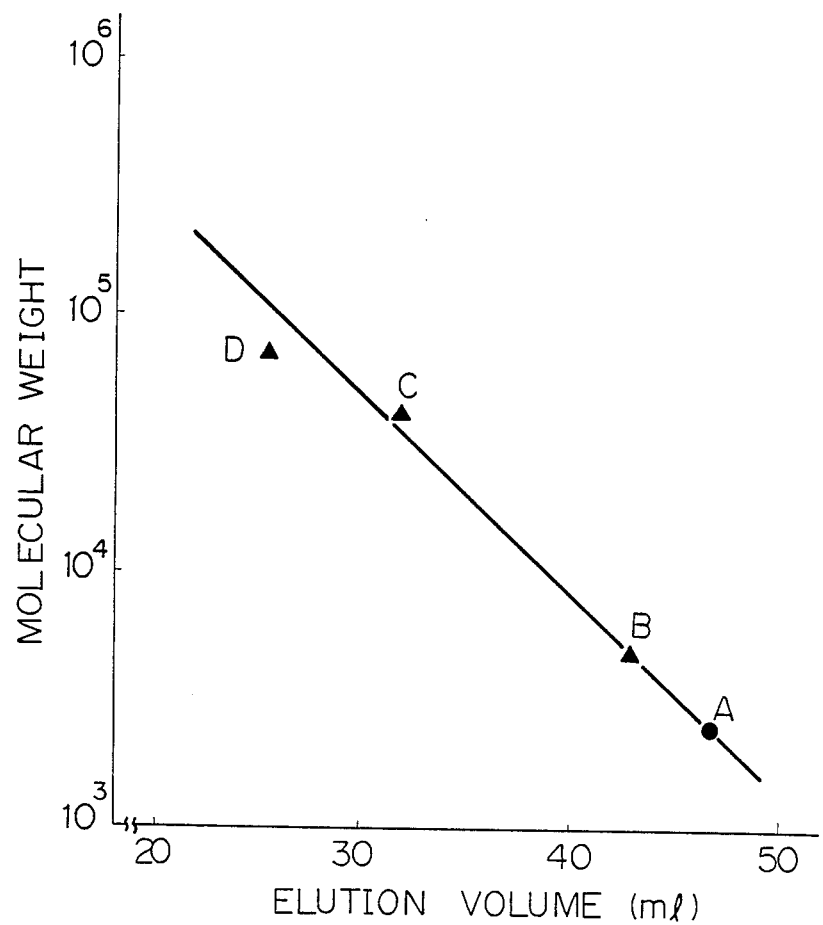
FIG. 1 illustrates the relationship between the molecular weight of materials and their elution volumes in gel filtration.

The present inventors have found that the novel RNA fractions obtained from microorganisms belonging to the genus Streptococcus can effectively reduce blood cholesterol and triglyceride, and that constituents extracted from so-called gastrointestinal bacteria are substantially nontoxic when orally administered.

The microorganisms used in the preparation of the product, the manufacturing methods, the physicochemical characteristics, and the pharmacological effects of the hypocholesterolemically and/or hypotriglyceridemically active RNA fractions according to the present invention will now be described in detail hereinbelow.

Microorganisms

1. Species

Microorganisms utilizable in the present invention belonging to the genus Streptococcus: such as Streptococcus faecium, Streptococcus faecalis, Streptococcus bovis, Streptococcus avium, Streptococcus durans, Streptococcus salivarius, Streptococcus mitis, Streptococcus equinus, and others are preferably shown.

Typical examples of such microorganisms have been deposited since July 15, 1982 in the Fermentation Research Institute (FRI) and transferred to FRI (i.e., International Depository Authority under Budapest Treaty in Japan). The deposition numbers are listed below in Table 1.

TABLE 1

| Strains | Deposition number |
| --- | --- |
| Streptococcus faecium | FERM BP-296 |
| Streptococcus faecalis | FERM BP-297 |
| Streptococcus avium | FERM BP-298 |
| Streptococcus salivarius | FERM BP-299 |
| Streptococcus durans | FERM BP-300 |
| Streptococcus mitis | FERM BP-301 |
| Streptococcus equinus | FERM BP-302 |

2. Microbiological Characteristics of Microorganisms

General microbiological characteristics

The microbiological characteristics of the microorganisms in the present invention are the same as those of known microorganisms belonging to the identical class.

That is, the general microbiological characteristics, cultivation methods and other properties correspond to those described in the following articles:
(1) Bergey's Manual of Determinative Bacteriology, 8th ed., 490-509 (1974)
(2) Int. J. Syst. Bact. 16, 114 (1966)
(3) Microbiol. Immunol. 25 (3), 257-269 (1981)
(4) J. Clin. Pathol. 33, 53-57 (1980)
(5) J. General Microbiol. 128, 713-720 (1982)
(6) Applied Microbiol. 23 (6), 1131-1139 (1972)

Typical microbiological characteristics of the above-exemplified strains according to the present invention are summarized in Table 2.

TABLE 2

| Characteristics | Strains FERM BP | | | | | | |
|---|---|---|---|---|---|---|---|
| | −296 | −297 | −298 | −299 | −300 | −301 | −302 |
| Shape of cell | | | | spheroid | | | |
| Gram stain | + | + | + | + | + | + | + |
| Hemolysis | α | α | α | α | α | α | α |
| Growth at 10° C. | + | + | ± | − | + | − | − |
| 45° C. | + | + | + | ± | + | ± | + |
| 50° C. | + | − | − | − | + | − | − |
| Thermal resistance at 60° C. for 30 min | + | + | + | − | + | − | − |
| Growth in culture medium at pH 9.6 | + | + | + | − | + | − | − |
| Methylene blue reduction | + | + | − | − | + | − | − |
| Liquefaction of gelatin | − | − | − | − | − | − | − |
| Growth in culture medium containing NaCl (6.5%) | + | + | − | − | + | − | − |
| Growth in culture medium containing bile (40%) | + | + | + | − | + | − | + |
| Productivity of ammonia | + | + | ND*2 | − | + | ± | − |
| Hydrolysis of hippuric acid | − | ± | − | − | + | − | − |
| Growth in culture medium containing tellurite | − | + | − | ND | − | ND | − |
| Growth in culture medium containing TTC*1 | − | + | − | ND | − | ND | − |
| Acid production from | | | | | | | |
| Glucose | + | + | + | + | + | + | + |
| Esculin | ± | + | + | + | ± | ND | + |
| Inulin | − | − | − | + | − | − | ± |
| Lactose | + | + | + | ± | + | ± | − |
| Glycerol | − | + | ± | − | − | − | − |
| Arabinose | + | − | + | − | − | − | − |
| Melezitose | − | + | ± | ND | − | ND | − |
| Sorbitol | − | + | + | − | − | − | − |
| Antigenic group | D | D | Q(D) | K | D | − | D |

*1 2, 3, 5-Triphenyltetrazolium chloride
*2 Not done

3. Cultivating methods

These microorganisms can be cultivated in a conventional manner. For example, the bacterial cells can be collected by stationary cultivation in a Rogosa broth medium (Efthymiou, C., and Hansen, P. A. (1962) An antigenic analysis of *Lactobacillus acidophilus*. J. Infect. Dis. 110: 258-267) having the following composition, and can be harvested by centrifugation of the culture.

| Composition of Rogosa Broth Medium | |
|---|---|
| Trypticase (BBL Microbiology Systems) | 10 g |
| Yeast extract (Difco Laboratories) | 5 g |
| Tryptose (Difco Laboratories) | 3 g |
| K$_2$HPO$_4$ | 3 g |
| KH$_2$PO$_4$ | 3 g |
| Triammonium citrate | 2 g |
| Tween 80 | 1 g |
| Glucose | 20 g |
| Cysteine hydrochloride | 0.2 g |
| Salt solution *1 | 5 ml |
| Distilled water | to 1 liter |
| (pH 7, heat sterillization at 121° C. for 15 minutes) | |

| *1 | | |
|---|---|---|
| MgSO$_4$—7H$_2$O | 11.5 g | |
| FeSO$_4$—7H$_2$O | 0.68 g | |
| MnSO$_4$-2H$_2$O | 2.4 g | |
| Distilled water | 100 ml | |

Preparation of the Hypocholesterolemically and/or Hypotriglyceridemically Active RNA Fractions An example of typical procedures for preparation of the hypocholesterolemically and/or hypotriglyceridemically active RNA fractions according to the present invention is given as follows:

1. Collection of Microorganisms

Each of the microbial strains shown above was inoculated into a Rogosa broth medium and incubated without agitation at 37° C. for 5 to 15 hours, to yield a subsequent culture broth at a certain viable bacterial cell concentration. The culture broth was continuously centrifuged at 12,000 rpm, and harvested bacterial cells were then washed 2 to 3 times in saline (0.85% NaCl).

2. Hydrochloric Acid Extraction

The washed cells were suspended in a 0.2N HCl solution and heat-treated at 100° C. for 5 to 15 minutes in a water bath. The heat-treated cell suspension was centrifuged at 100,000 Xg for 15 minutes, and the supernatant neutralized with NaOH solution and dialysed.

The inner fluid was lyophilized and suspended in trichloroacetic acid (TCA) solution, and the solution kept at 4° C. for 3 to 5 hours. Then, after centrifugation at 15,000 Xg for 10 to 20 minutes, the supernatant was neutralized with NaOH solution and dialysed again, and the inner fluid was lyophilized.

3. Isolation and Purification of RNA Fractions

Gel filtration of the above lyophilized materials was carried out using a Sephadex G-75 (Pharmacia Fine Chemicals) and every ca. 10 ml of the eluate was taken to isolate the fractions which have a peak absorbance ($A_{660}$ nm) in the orcinol method. The isolated fractions were purified by Sephadex G-75 (Pharmacia Fine Chemicals) again to obtain the desired active RNA fractions.

In general, this hypocholesterolemically and/or hypotriglyceridemically active RNA fractions can be prepared according to the physicochemical characteristics thereof, mentioned below, by many of the isolation and purification procedures already widely employed in the field concerned, such as precipitation-dissolution and extraction, solvent extraction, dialysis, column chromatography, electrophoresis, gel filtration, or any combination of these procedures. Therefore, the present invention is by no means limited to a specified procedure.

That is, the preparation of the present invention is related to the preparation methods of hypocholesterolemically and/or hypotriglyceridemically active products, which are composed of RNA fractions and obtained from microorganisms belonging to the genus Streptococcus, because the pharmacological activity is found in the RNA fractions.

Physicochemical Characteristics of the Hypocholesterolemically and/or Hypotriglyceridemically Active RNA Fractions The physicochemical and physiological characteristics of the hypocholesterolemically and/or hypotriglyceridemically active RNA fractions of the present invention are as follows.

1. Chemical Nature and Solubility

The lyophilized sample of the RNA fractions of the present invention is light yellow and is soluble in water, 1N NaOH and 1N HCl solution, insoluble in alcohol and ether, and slightly soluble in benzene.

2. Molecular Weight

Gel filtration was carried out with a 0.05M Tris-hydrochloric acid buffer (pH 7.4) as the eluate and using Sephacryl S-200 (Pharmacia Fine Chemicals). The absorbance by phenol-$H_2SO_4$ method ($A_{490}$ nm), $A_{280}$ nm, and $A_{260}$ nm of each fraction obtained above was measured and converted into a glucose amount using dextrans as standards. The results were shown in FIG. 1, where the abscissa and ordinate indicate elution volume (ml) and molecular weight, respectively. Point A shows the molecular weight of the RNA fraction of the present invention. Points B, C, and D correspond to the molecular weights 5,000, 40,000 and 70,000 of standard dextrans, respectively.

The molecular weight of the sample was thus estimated to be ca. 2,700.

3. Infrared Absorption Spectrum

Figure 2:
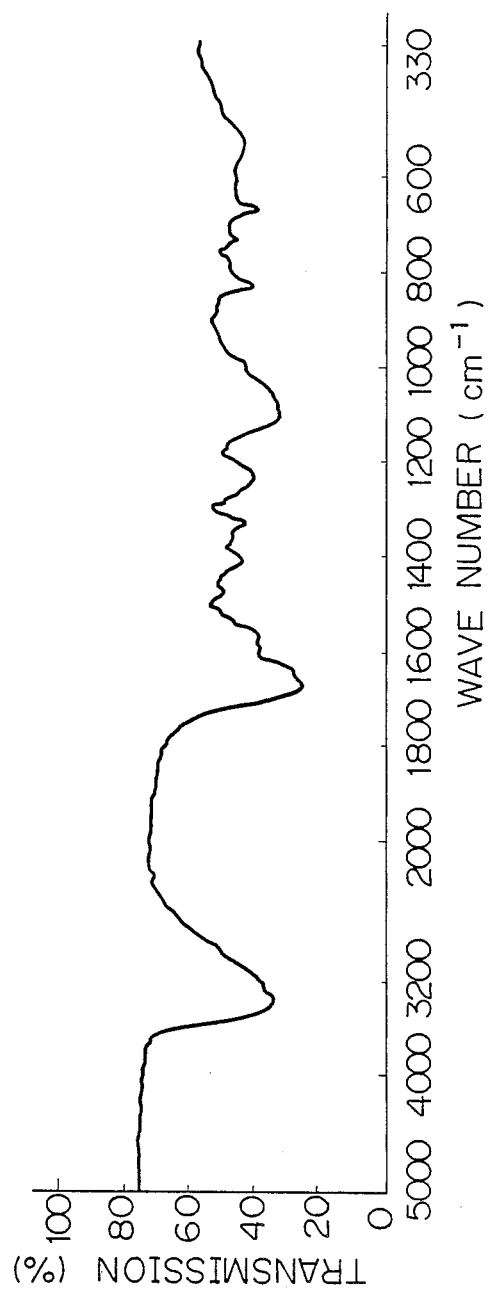
FIG. 2 illustrates an infrared absorption spectrum profile of the hypocholesterolemically and/or hypotriglyceridemically active RNA fractions of the present invention.

The infrared absorption spectrum of the hypocholesterolemically and/or hypotriglyceridemically active RNA fractions, measured by a KBr tablet infrared spectrometer (model JASCO A-302, Japan Spectroscopic Co., Ltd.) is shown in FIG. 2, where the abscissa and ordinate indicate the wave number and percent transmission, respectively.

4. Base Composition of the Nucleic Acid

The base composition of the nucleic acid, which was hydrolyzed (and neutralized with HCl solution) with 1 ml of a 0.3N KOH solution at 37° C. for 18 hrs, was estimated at U (uracil):G (guanine):C (cytosine):A (adenine)=13.0:16.0:16.0:10.0 by high speed liquid chromatography (1).

(1) The high speed liquid chromatography (HPLC) analyses were made under the condition shown below.

| | |
|---|---|
| HPLC: | Hitachi 655 Liquid Chromatograph |
| Detector: | Hitachi 638-0410 |
| Wavelength: | 270 nm |
| Range: | 1.28 AUFS |
| Column: | Partisil 10SAX |
| Eluate: | 0.05 M $KH_2PO_4$ buffer (pH 3.05) |
| Flow rate: | 1.0 ml/min |
| Standard materials: | 2'(3')-AMP, free lot No. 1 |
| | 2'(3')-GMP, free lot No. 40323 |
| | 2'(3')-CMP, free lot No. 521 |
| | 2'(3')-UMP, free lot No. 40629 |

5. Physiological Characteristics

The hypocholesterolemically and/or hypotriglyceridemically active RNA fractions have an activity which will reduce the blood cholesterol and triglyceride levels in mammals when administered orally.

Pharmacological Actions

1. As shown in each example hereinbelow, the present antiatherosclerotic drug composed of the hypocholesterolemically and/or hypotriglyceridemically active RNA fractions of the present invention is extremely effective in reducing the blood cholesterol and triglyceride levels in mammals. Accordingly, this drug is useful as a therapeutic or preventive medicine for diseases to which these parameters of the serum are closely related, such as atherosclerosis, hyperlipidemia, cerebral atherosclerosis, hyperlipoproteinemia, xanthomatosis, cholecystolithiasis, hepato-cholepathia, nephropathy (nephrosis syndrome), hypertension, diabetes, cardiopathia, endocrinism, hypothyreosis, adiposis, and others.

The preparation of the present invention can be administered to mammals via oral, intraperitoneal, intravenous, and other administration routes. The amount per dosage is preferably about 10 μg to 0.5 g/kg body weight. An oral administration of about 0.1 mg to 50 mg/kg body weight is preferred. Any drug form of the present invention can be chosen and used as a solution in physiological saline and others, injections, lyophilized powder, etc., suppository, entericcoated tablets, sublingual tablets, granules, tablets, capsules, etc., with appropriate carriers, diluent bases, diluents, etc.

2. Acute Toxicity

As shown in the examples hereinbelow, an LD50 of the hypocholesterolemically and/or hypotriglyceridemically active RNA fractions according to the present invention is more than 1,260 mg/kg body weight, intraperitoneally in mice. The substance is substantially nontoxic upon oral administration.

EXAMPLES

The present invention will now be further shown by, but is by no means limited to, the following examples.

EXAMPLE 1

Preparation and purification of the hypocholesterolemically and/or hypotriglyceridemically active RNA fractions.

Figure 3:
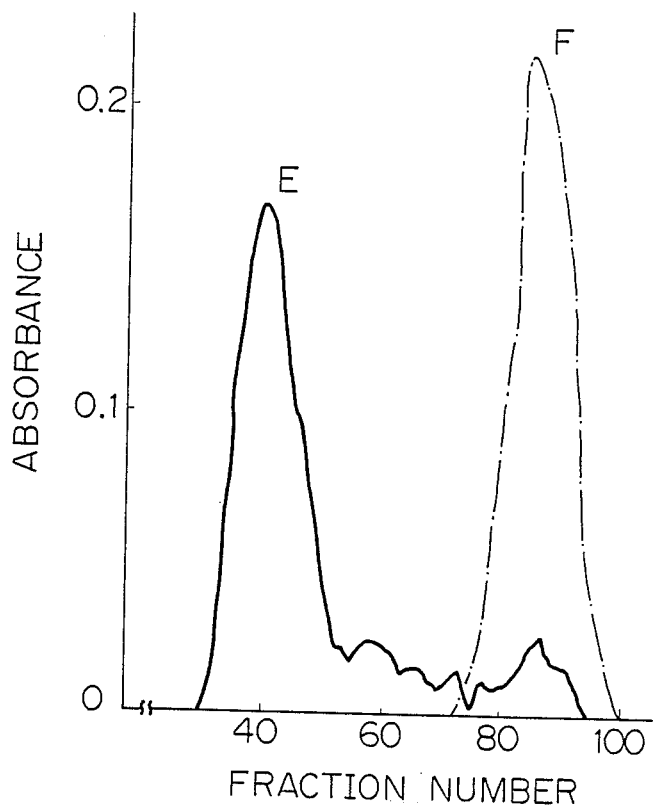
FIG. 3 illustrates the elution patterns of gel filtration of the hypocholesterolemically and/or hypotriglyceridemically active RNA fractions of the present invention.

One hundred liters of Rogosa broth medium inoculated with *Streptococcus faecium* ADV1009 (FERM BP-296) were incubated at 37° C. for 10 hrs without agitation. The obtained 320 g of wet bacterial cells were added with 0.8 l of 0.2N HCl solution and heat-treated at 100° C. for 10 minutes in a water bath. The heat-treated cell suspension was centrifuged at 100,000 Xg for 15 minutes. The obtained supernatant was neutralized with an NaOH solution, and dialysed (cut-off of molecular weight 3,500) using a Spectrapor dialysing membrane (Spectrum Medical Industries, Inc.). The obtained inner fluid was lyophilized, suspended in 8% TCA solution, and kept at 4° C. for 4 hrs. The treated sample was centrifuged at 15,000 Xg for 15 minutes, and the supernatant was neutralized with an NaOH solution and dialysed (cut-off of molecular weight 3,500) again. After lyophilization of the inner fluid, gel filtration was carried out with 0.2M pyridineacetic acid buffer (pH 5.02) as the eluate and using a Sephadex G-75 column of 4×100 cm (Pharmacia Fine Chemicals). About 10 ml fractions of gel filtration of the sample were taken and assayed by the phenol-$H_2SO_4$ method, the orcinol method, and the Lowry method. The results were shown in FIG. 3, where the abscissa and ordinate indicate the fraction number and the absorbance, respectively. The E shows values by the phenol-$H_2SO_4$ method ($A_{490}$ nm) and the F by the orcinol method ($A_{660}$ nm). No absorbance was shown in all the fractions by the Lowry method ($A_{750}$ nm).

The fraction F was purified by Sephadex G-75 gel filtration again, and the desired active RNA fractions of 1.84 g were obtained.

The chemical composition of the RNA fractions was shown in Table 3.

TABLE 3

| Constituents | Protein | Sugar | | RNA | DNA |
|---|---|---|---|---|---|
| Methods | Lowry method | Phenol-$H_2SO_4$ method | Anthron-$H_2SO_4$ method | Orcinol method | Diphenylamine method |
| % | 4.8 | 18.4* | 3.4 | 99.1 | 2.9 |

*The phenol-$H_2SO_4$ method shows a higher value of sugar than the Anthron-$H_2SO_4$ method because of a reaction with the sugar residues of nucleic acids.

On the other hand, it was assured that same RNA fractions were obtained as in Example 1 from the other strains shown in Table 1.

The physicochemical characteristics of the RNA fractions were as shown above.

EXAMPLE 2

Pharmacological effect of the hypocholesterolemically and/or hypotriglyceridemically active RNA fractions

1. Hypocholesterolemic and/or Hypotriglyceridemic Activity (I)

Solutions containing the equivalent amount of 10 mg/kg body weight per ml of the lyophilized hypocholesterolemically and/or hypotriglyceridemically active RNA fractions were prepared. These samples were orally administered (1 ml/day/rat) to conventional rats (18 week-old, male, average body weight 242 g, 5 rats per group) and conventional and germfree mice (10 week-old, male, average body weight 19.1 g, 5 mice per group). The rats and mice were bred for 8 to 12 weeks. Arterial blood was then collected from the abdominal aorta of these animals and serum samples were separated by centrifugation from the whole blood. The cholesterol and triglyceride levels were determined by using *Choleskit* (Kanto Chemical Co., Inc., Zurkowski method) and *Triglyceride TG WAKO* (Wako Pure Chemical Industries, Ltd., acetyl-acetone extraction method), respectively.

The results are summarized in Table 4. The values listed in the table are the reduction rate (%) from the values in the control groups to which no sample is dosed. The composition (% by weight) of the diet, given ad libitum, is shown in Table 5.

TABLE 4

| Animals (administration period) | Cholesterol Reduction rate (%) | Triglyceride Reduction rate (%) |
|---|---|---|
| Conventional rats (12 weeks) | 21.3 | 24.6 |
| Conventional mice (8 weeks) | 24.6 | 35.5 |
| Germfree mice (8 weeks) | 33.1 | 38.5 |

TABLE 5

| Composition | Weight (%) |
|---|---|
| Milk casein | 20 |
| Soybean oil | 10 |
| Wheat starch | 61 |
| Minerals *1 | 4 |
| Vitamin mixture *2 | 2 |
| Powdered filter paper (cellulose) | 3 |

| *1 | Phillips-Hart salt | *(Iwai Kagaku Co., Ltd.) |
|---|---|---|
| | $K_2HPO_4$ | 322 (g/1,000 g) |
| | $CaCO_3$ | 300 |
| | NaCl | 167 |
| | $MgSO_4$ | 102 |
| | $Ca_2P_2O_7$ | 75 |
| | Ferric citrate | 27.5 |
| | $CuSO_4.5H_2O$ | 0.3 |
| | $ZnCl_2$ | 0.25 |
| | $MnSO_4.4H_2O$ | 5.1 |
| | KI | 0.8 |
| | $CoCl_2.6H_2O$ | 0.05 |

*Phillips, P. H. and Hart, E. B., The effect of organic dietary constituents upon TABLE 5-continued

| Composition | Weight (%) |
|---|---|
| chronic fluorine toxicosis in the rat, J. Biol. Chem., 109, 657, (1935) | |
| *2 Panvitan powder (Takeda Chemical Industries, Ltd.) | 20 (g/100 g) |
| Choline chloride | 10 |
| Calcium pantothenate | 0.15 |
| Pyridoxine hydrochloride | 0.006 |
| Inositol | 1.0 |
| Wheat starch | 68.8 |

2. Hypocholesterolemic and/or Hypotriglyceridemic Activity (II)

The above-mentioned samples were orally administered (1 ml/day/rat) to conventional rats (18 week-old, male, average body weight 235 g, 5 rats per group) and conventional and germfree mice (10 week-old, male, average body weight 23 g, 5 mice per group) for 12 weeks. The blood cholesterol and triglyceride levels were determined as mentioned above. The results are shown in Table 6.

The terms "cholesterol-loaded" and "fructose-loaded" in the table mean the addition of 1% cholesterol into the above-mentioned diet and the substitution of fructose for the total amount of wheat starch in the above-mentioned diet, respectively. The values in the table are the reduction rate (%) from the values of the no dosage control group.

TABLE 6

| Animals | Cholesterol Reduction rate (%) | Triglyceride Reduction rate (%) |
|---|---|---|
| Germfree mice *1 | 30.4 | 35.3 |
| Conventional mice *1 | 31.6 | 36.9 |
| Conventional rats *1 | 32.6 | 39.4 |
| Conventional rats *2 | 28.6 | 43.5 |

*1 Cholesterol-loaded diet
*2 Fructose-loaded diet

3. Hypocholesterolemic and/or Hypotriglyceridemic Activity (III)

Solutions containing the equivalent amount of 10 mg/kg body weight of the RNA fractions were orally administered (1.0 ml/day/rat) for 2 weeks to hyperlipidemic rats (8 week-old, male, average body weight 213 g, 5 rats per group) fed a cholesterol-loaded diet. The serum cholesterol and triglyceride levels were determined as mentioned above. The results are shown in Table 7. The values of the administration group are the cholesterol and triglyceride reduction rate (%) to the no dosage control group.

TABLE 7

| Animals | Cholesterol Reduction rate (%) | Triglyceride Reduction rate (%) |
|---|---|---|
| Administered | 29.8 | 36.3 |
| Control | 0 | 0 |

4. Dose Response

Solutions containing 0.1 mg–20 mg/ml of the hypocholesterolemically and/or hypotriglyceridemically active RNA fractions were orally administered (1 ml/day/rat) to conventional rats (6 week-old, male, average body weight 207 g, 5 rats per group) for 4 weeks. The blood cholesterol and triglyceride levels were determined as mentioned above (control group was no dosed group). The results are shown in Table 8.

TABLE 8

| Dosage (mg/rat) | Cholesterol Reduction rate (%) | Triglyceride Reduction rate (%) |
|---|---|---|
| Control | 0 | 0 |
| 0.1 | 6.9 | 11.1 |
| 1 | 14.9 | 21.5 |
| 10 | 39.8 | 42.6 |
| 20 | 42.6 | 45.3 |

5. Acute Toxicity

Physiological saline samples (0.5 ml/mouse) containing 1, 10, and 100 mg of the hypocholesterolemically and/or hypotriglyceridemically active RNA fractions were intraperitoneally administered to ICR mice (6 week-old male, average body weight 28.4±0.5 g, 10 mice per group). The thanatobiologic observation of mice was carried out for 14 days. The control material was physiological saline.

The LD50 value calculated according to the Behrens-Kärber method was more than 1,260 mg/kg body weight. The substance was substantially nontoxic on oral administration.

6. Pharmaceutical preparations (1) A 25 mg amount of the purified hypocholesterolemically and/or hypotriglyceridemically active RNA fractions were uniformly mixed with 275 mg of purified starch powder, and the tablets for oral administration were then formed. Each tablet corresponded to a dosage of $2 \times 10^{10}$ heat-treated cells/kg body weight for an adult having a body weight of 50 kg.

(2) The hypocholesterolemically and/or hypotriglyceridemically active RNA fractions are uniformly mixed with diluent bases such as calcium carbonate, lactose, etc., lubricants such as stearic acid, talcum, etc., and other additives, and the tablets then formed for oral administration. The daily dosage of the hypocholesterolemically and/or hypotriglyceridemically active RNA fractions is usually 0.1 mg–50 mg/kg body weight.

(3) The hypocholesterolemically and/or hypotriglyceridemically active RNA fractions (900 mg) were suspended and dissolved in distilled water (30 ml) sweetened with syrup, and syrups were then formed.

We claim:

1. A method for reducing blood cholesterol in mammals comprising orally administering to the mammals a hypocholesterolemically effective amount of hypocholesterolemically active RNA fractions having the following characteristics:
  (a) Molecular weight by gel filtration: 2,000±1,000
  (b) Base composition ratio of nucleic acid:uracil:-guanine:cytosine:adenine=13.0:16.0:16.0:10.0
  (c) Infrared absorption spectrum: shown in FIG. 2
  (d) Physiological characteristics: having hypocholesterolemic activity in mammals.

2. A method as claimed in claim 1, wherein said hypocholesterolemically active RNA fractions are derived from microorganisms belonging to the genus Streptococcus.

3. A method as claimed in claim 2, wherein said microorganism is at least one member selected from the group consisting of S. faecium, S. faecalis, S. avium, S. bovis, S. salivarius, S. durans, S. mitis, and S. equinus.

4. A method as claimed in claim 2, wherein said microorganism is at least one strain selected from the group consisting of *S. faecium*, FERM BP-296, *S. faecalis*; FERM BP-297, *S. avium* FERM BP-298, *S. salivarius* FERM BP-299, *S. durans* FERM BP-300, *S. mitis* FERM BP-301, and *S. equinus* FERM BP-302.

5. A method for reducing the blood triglyceride in mammals comprising orally administering to the mammals a hypotriglyceridemically effective amount of hypotriglyceridemically active RNA fractions having the following characteristics:
  (a) Molecular weight by gel filtration: $2,000 \pm 1,000$
  (b) Base composition ratio of nucleic acid:uracil:guanine:cytosine:adenine = 13.0:16.0:16.0:10.0
  (c) Infrared absorption spectrum: shown in FIG. 2
  (d) Physiological characteristics: having a hypotriglyceridemic activity in mammals.

6. A method as claimed in claim 5, wherein said hypotriglyceridemically active RNA fractions are derived from microorganisms belonging to the genus Streptococcus.

7. A method as claimed in claim 6, wherein said microorganism is at least one member selected from the group consisting of *S. faecium*, *S. faecalis*, *S. avium*, *S. bovis*, *S. salivarius*, *S. durans*, *S. mitis*, and *S. equinus*.

8. A method as claimed in claim 6, wherein said microorganism is at least one strain selected from the group consisting of *S. faecium* FERM BP-296, *S. faecalis* FERM BP-297, *S. avium* FERM BP-298, *S. salivarius* FERM BP-299, *S. durans* FERM BP-300, *S. mitis* FERM BP-301, and *S. equinus* FERM BP-302.

* * * * *